United States Patent
Bianchi et al.

(10) Patent No.: US 7,182,781 B1
(45) Date of Patent: *Feb. 27, 2007

(54) CERVICAL TAPERED DOWEL

(75) Inventors: John R. Bianchi, Alachua, FL (US); Kevin C. Carter, Alachua, FL (US)

(73) Assignee: Regeneration Technologies, Inc., Alachua, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/704,299

(22) Filed: Nov. 1, 2000

Related U.S. Application Data

(60) Provisional application No. 60/186,312, filed on Mar. 2, 2000.

(51) Int. Cl.
*A61F 2/44* (2006.01)
*A61B 17/56* (2006.01)

(52) U.S. Cl. .................. 623/17.11; 623/17.16

(58) Field of Classification Search ............. 623/17.11, 623/17.16, 17.12, 17.13, 17.14, 17.15, 16.11, 623/18.11, 11.11, 23.63, 919, 901, 925; 606/60, 61, 77
See application file for complete search history.

(56) References Cited

U.S. PATENT DOCUMENTS

| | | |
|---|---|---|
| 4,721,096 A | 1/1988 | Naughton et al. |
| 4,878,915 A * | 11/1989 | Brantigan ................. 623/17.11 |
| 4,963,489 A | 10/1990 | Naughton et al. |
| 5,197,985 A | 3/1993 | Caplan et al. |
| 5,486,359 A | 1/1996 | Caplan et al. |
| 5,591,625 A | 1/1997 | Gerson et al. |
| 5,593,409 A * | 1/1997 | Michelson .................. 606/61 |
| 5,609,635 A | 3/1997 | Michelson |
| 5,609,636 A * | 3/1997 | Kohrs et al. ............. 623/17.11 |
| 5,669,909 A | 9/1997 | Zdeblick et al. |
| 5,733,542 A | 3/1998 | Haynesworth et al. |
| 5,736,396 A | 4/1998 | Bruder et al. |
| 5,782,919 A | 7/1998 | Zdeblick et al. |
| 5,811,094 A | 9/1998 | Caplan et al. |
| 5,814,084 A * | 9/1998 | Grivas et al. ............. 623/23.48 |
| 5,827,735 A | 10/1998 | Young et al. |
| 5,902,741 A | 5/1999 | Purchio et al. |
| 5,906,616 A * | 5/1999 | Pavlov et al. .................. 606/61 |
| 5,906,934 A | 5/1999 | Grande et al. |
| 5,908,784 A | 6/1999 | Johnstone et al. |
| 5,942,255 A | 8/1999 | Klesges |

(Continued)

FOREIGN PATENT DOCUMENTS

| DE | 3505567 | 6/1986 |
|---|---|---|

(Continued)

*Primary Examiner*—Pedro Philogene
(74) *Attorney, Agent, or Firm*—McAndrews, Held & Malloy, Ltd.

(57) ABSTRACT

Disclosed herein are biomedical implants, and methods of using same, that are derived from bone. Particularly exemplified are implants having a tapered dowel shape that are useful for implantation in the spine, and especially in the cervical region of the spine. The taper of the implants disclosed herein provides an advantage over conventional implants, as it creates the proper support and angulation to maintain the proper curvature of the spine. Optionally, the implants taught herein are associated with osteogenic materials or other biomedical substances.

7 Claims, 15 Drawing Sheets

U.S. PATENT DOCUMENTS

| | | | |
|---|---|---|---|
| 5,951,560 A | 9/1999 | Simon et al. | 606/73 |
| 5,962,325 A | 10/1999 | Naughton et al. | |
| 6,102,948 A * | 8/2000 | Brosnahan, III | 623/17.16 |
| 6,111,164 A * | 8/2000 | Rainey et al. | 623/17.11 |
| 6,165,219 A * | 12/2000 | Kohrs et al. | 623/17.11 |
| 6,174,311 B1 * | 1/2001 | Branch et al. | 606/61 |
| 6,200,347 B1 * | 3/2001 | Anderson et al. | 323/16.11 |
| 6,210,412 B1 * | 4/2001 | Michelson | 606/61 |
| 6,258,125 B1 * | 7/2001 | Paul et al. | 623/17.11 |
| 6,261,586 B1 * | 7/2001 | McKay | 424/423 |
| 6,277,149 B1 * | 8/2001 | Boyle et al. | 623/17.16 |
| 6,458,158 B1 * | 10/2002 | Anderson et al. | 623/16.11 |
| 6,494,883 B1 * | 12/2002 | Ferree | 606/61 |
| 6,527,805 B2 * | 3/2003 | Studer et al. | 623/17.16 |
| 6,558,423 B1 * | 5/2003 | Michelson | 623/17.11 |
| 6,652,584 B2 * | 11/2003 | Michelson | 623/17.11 |

FOREIGN PATENT DOCUMENTS

| | | |
|---|---|---|
| EP | 0517030 | 12/1992 |
| EP | 0734703 | 10/1996 |
| WO | WO 96/40019 | 12/1996 |
| WO | WO 97/25945 | 7/1997 |
| WO | WO 98/38924 | 9/1998 |
| WO | WO 98/40113 | 9/1998 |
| WO | WO 99/09914 | 3/1999 |

* cited by examiner

CERVICAL TAPERED DOWEL

CROSS-REFERENCE TO RELATED APPLICATION

This application claims the benefit under 35 USC § 119(e) of Provisional Application No. 60/186,312 filed Mar. 2, 2000.

BACKGROUND OF THE INVENTION

Many advances are being made in the field of orthopedic implants, especially in relation to the treatment of diseases, injuries or defects of the spine. For example U.S. Pat. No. 5,814,084 ('084 patent) discloses a diaphysial cortical dowel designed for vertebral fusions, which represents a marked improvement over the conventional implants to date. The dowel of the '084 patent is made of bone, thus it is remodeled by the patient and does not suffer from many of the drawbacks observed with metals and synthetics, e.g., inflammation, weakening of surrounding tissues, and antigenicity. The subject invention builds on the successes in this field, by providing an implant that is shaped for implantation at certain locations of the spine and aids in maintaining the proper curvature of the spine as well.

SUMMARY OF THE INVENTION

The subject invention relates to an implant made of bone that comprises an elongated body having a first and second ends, wherein the elongated body tapers down its length from a point on or proximate to the first end to the second end or a point proximate thereto. The term "proximate" as used herein is intended to mean a point or region located on the elongated body of the implant that is closer to the end to which it corresponds than the opposing end. For example, proximate to said first end would mean a point or region closer to the first end than the second end. Specifically exemplified is an implant substantially shaped in the form of a dowel.

In a another embodiment, the subject implant has a channel formed therethrough to allow for the disposition therein of osteogenic and other biomedical substances. Optionally, the implant has perforations or holes to facilitate the release and delivery of such substances.

In an alternative embodiment, the subject implant comprises a plurality of sections that can be assembled and secured together. As with the other embodiments described herein, the assembled implant can comprise a channel for the disposition of osteogenic and other substances.

The subject implant is designed for implantation into the spine during spinal surgeries, especially spinal fusions (arthrodesis). The taper of the subject invention provides an advantage over conventional implants, as it creates the proper support and angulation to maintain the proper curvature of the spine (lordosis). Accordingly, a further embodiment of the subject invention pertains to a method of performing spinal surgery comprising implanting the subject implant into the intervertebral space in a spinal fusion procedure. Further, the novel use of bone as the material for producing the subject implant provides other advantages. Such advantages include the provision of an implant that is remodeled by the body into autogenous bone, and thereby incorporated into the existing bone structure. This leads to a more desirable result with respect to the strength and integrity of the implant. Further, the subject implant does not have the problem of inflammation at the implant site that is often caused by non-remodelable materials, such as metals or plastics. This inflammation can lead to deterioration of the bone surrounding the implant site, which can cause complications and necessitate follow-up surgeries.

BRIEF DESCRIPTION OF THE DRAWINGS

FIG. 2A shows a side view of this embodiment and FIG. 2B depicts a close-up of the threaded surface.

FIG. 3A shows a side view capturing the channel of the implant. FIG. 3B represents a close-up of the threads machined on the exterior of the implant. FIG. 3C represents an end-view of this embodiment. FIG. 3D shows a side-view of this embodiment that is rotated as to show the side walls of the implant adjacent to the channel.

FIG. 4A shows a side view which depicts the channel and wedge-like end. FIG. 4B shows a perspective view of this embodiment. FIG. 4C shows an end-view of the wedge-like end. FIG. 4D shows a side view that is rotated as to show the side walls of the implant adjacent to the channel.

FIG. 6A is a perspective view of this embodiment. FIG. 6B is a side view of this embodiment. FIG. 6C is an end-view of the wider end of this embodiment.

FIG. 9A is a side view of an embodiment that has a channel and smooth exterior. FIG. 9B is an end view of the embodiment shown in FIG. 9A. FIG. 9C is a side view of the embodiment of FIG. 9A which has a threaded exterior surface.

DESCRIPTION OF THE PREFERRED EMBODIMENTS

Turning now to the drawings, FIGS. 1A–B show an example of a bone block 100 that is then tapered according to the teachings of the subject invention. The dashed lines A depict the tapering of the bone block, which can be accomplished by conventional machining methods, e.g., with a lathe and in particular, a CNC lathe. Holes 105 are drilled into the bone block via a drill to engage a securing device for positioning of the implant of the subject invention into the spine. Preferably, 4 holes are drilled in a square configuration suitable for engaging a specially adapted securing device having four prongs for insertion into holes 105. Typically, the subject implant is secured by rotation. See FIG. 1B. Machining attachment hole 110 is formed in the bone block 100 which provides a means for the block to be positioned in a machine such as a mill or lathe to hold the block steady during machining, to ensure proper alignment, and to permit rotation of the workpiece during machining.

Figure 1:
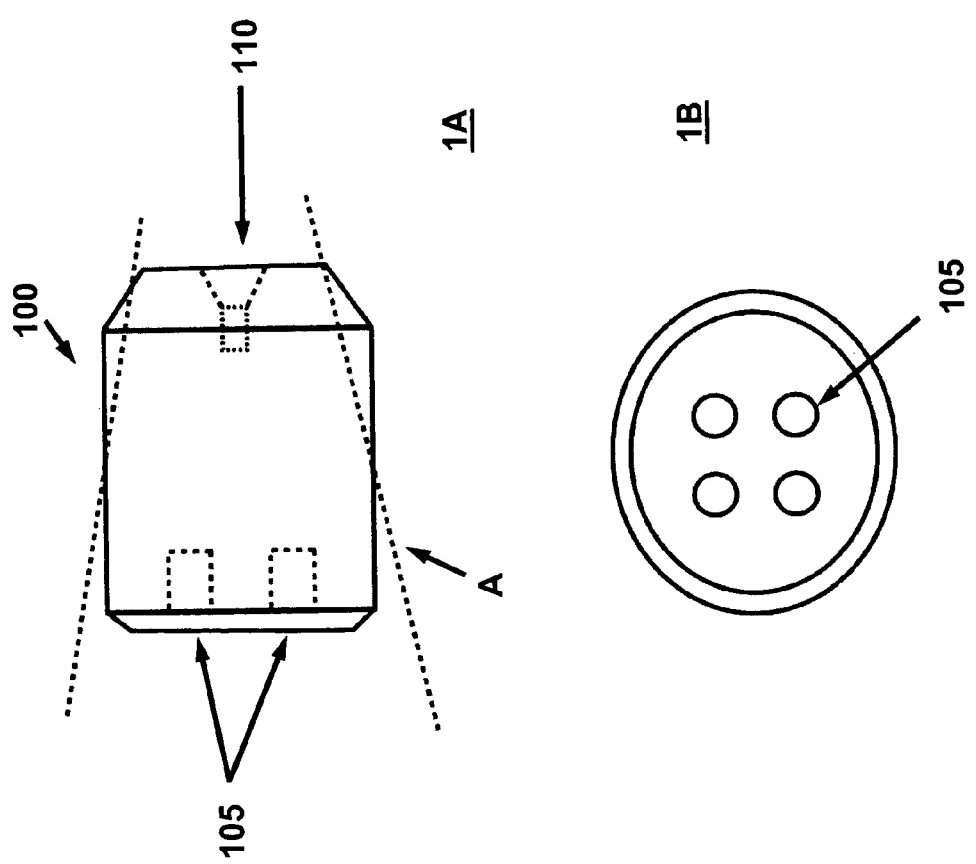
FIG. 1 shows side view (FIG. 1A) and an end view (FIG. 1B) of a starting bone block that is machined to obtain a tapered implant according to the teachings herein, and which comprises holes to engage a securing device.
Figure 2:
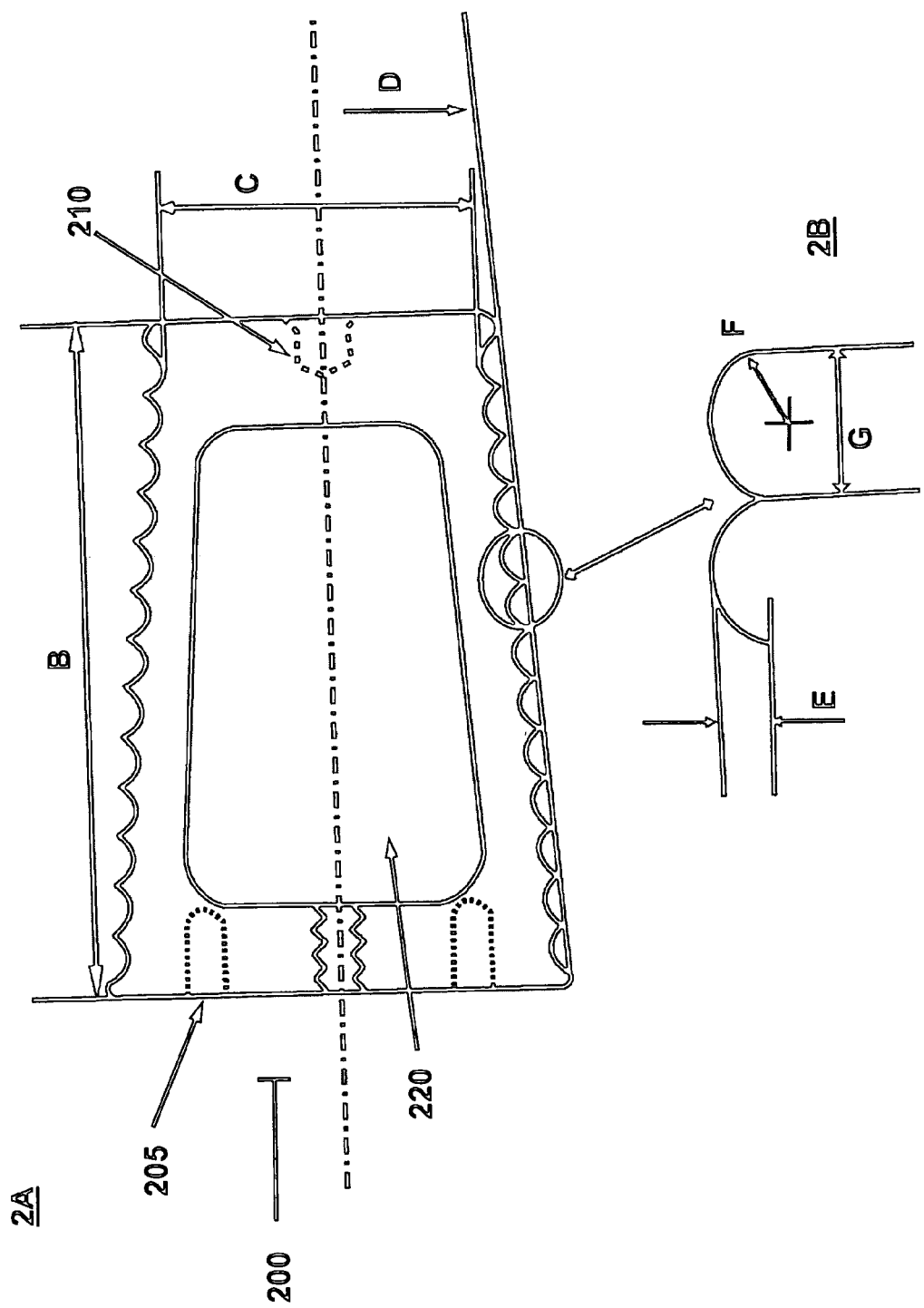
FIG. 2 shows another embodiment of the subject implant that has a threaded outer surface and comprises a channel that provides a space to dispose biologically active substances.

In FIGS. 2A–B, there is shown another embodiment 200 of the subject implant. As shown in FIG. 1, embodiment 200 comprises holes 205 for engaging a securing and driving device. Further, this embodiment comprises a channel 220 that preferably transverses completely through the implant. Channel 220 provides a space into which an osteogenic material can be disposed to aid in the healing and bone formation process. Also, the inventors have discovered that provision of the channel 220 aids in release of bone morphogenetic proteins (BMP) naturally present in the bone used for producing the subject implant and better contact of adjacent vertebrae with the osteogenic material within said dowel. In addition, in embodiments of this invention, channels, pores or the like may be formed, preferably connecting the exterior of the implant with the channel, to better induce seepage of growth factors from the osteogenic material in the channel or in the bone into the surrounding tissue. Embodiment 200 also comprises a machining attachment hole 210. Various dimensions of the implant are noted in FIGS. 2A–B, represented by the letters B–G. The skilled artisan will readily appreciate that these dimensions can be adapted to suit various sized patients, including infants, children, and adults. The following values are to be viewed as preferred values. Length B can range from about 5 to about 25 mm, and preferably from about 10 to about 15 mm. The root diameter C can range from about 3 to about 15 mm, and preferably from about 4 to about 11 mm. The taper angle D can range from about 1 to about 8 degrees, and preferably from about 3 to about 5 degrees. E can range from about 0.3 mm to about 1 mm, and preferably from about 0.4 mm to about 0.6 mm. The radius F of the thread profile can range from about 0.3 mm to about 1.3 mm, and preferably from about 0.5 mm to about 0.9 mm. The pitch G of the thread profile can range from about 0.08 to about 2 mm, and preferably from about 1 mm to about 1.8 mm.

Figure 3:
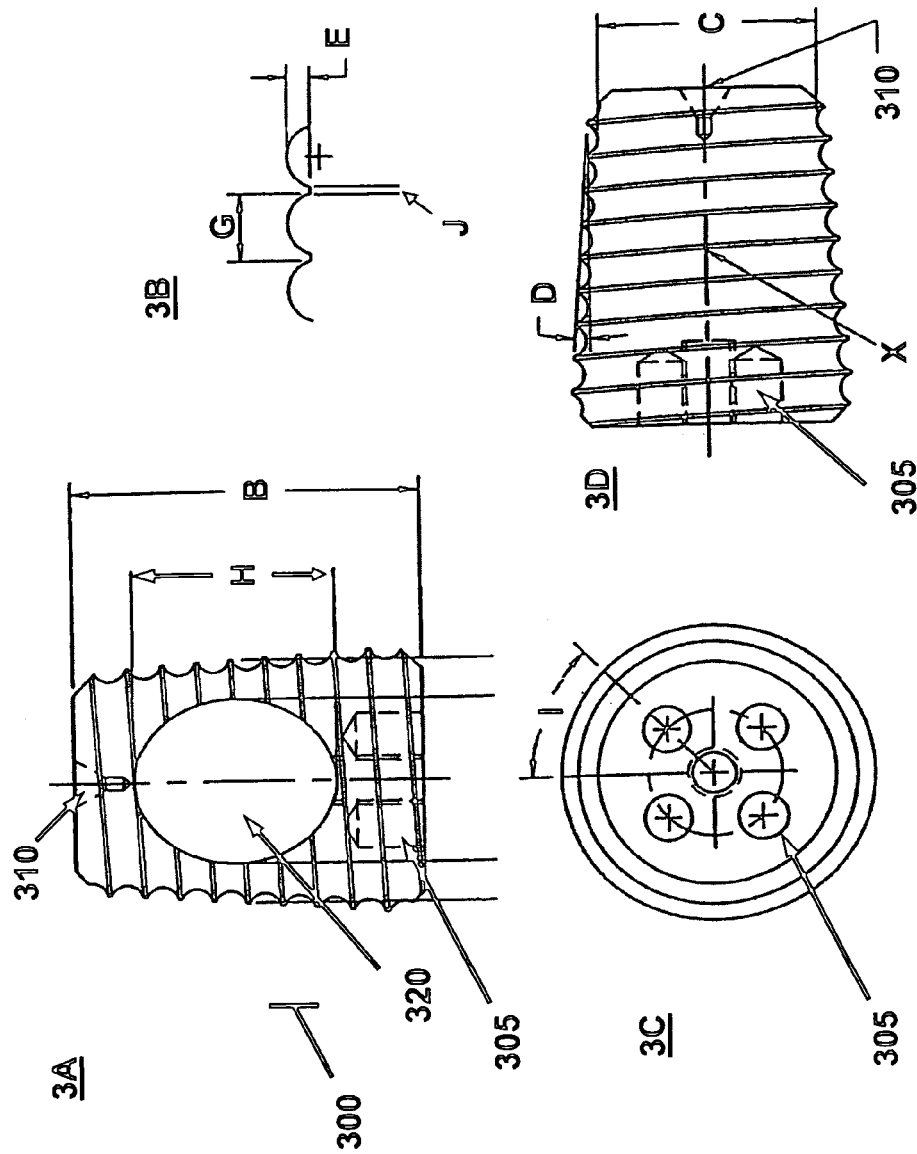
FIG. 3 shows another embodiment of the subject implant that comprises an oval channel and whose threads are slightly modified compared to the threads shown in FIG. 2.
Figure 4:
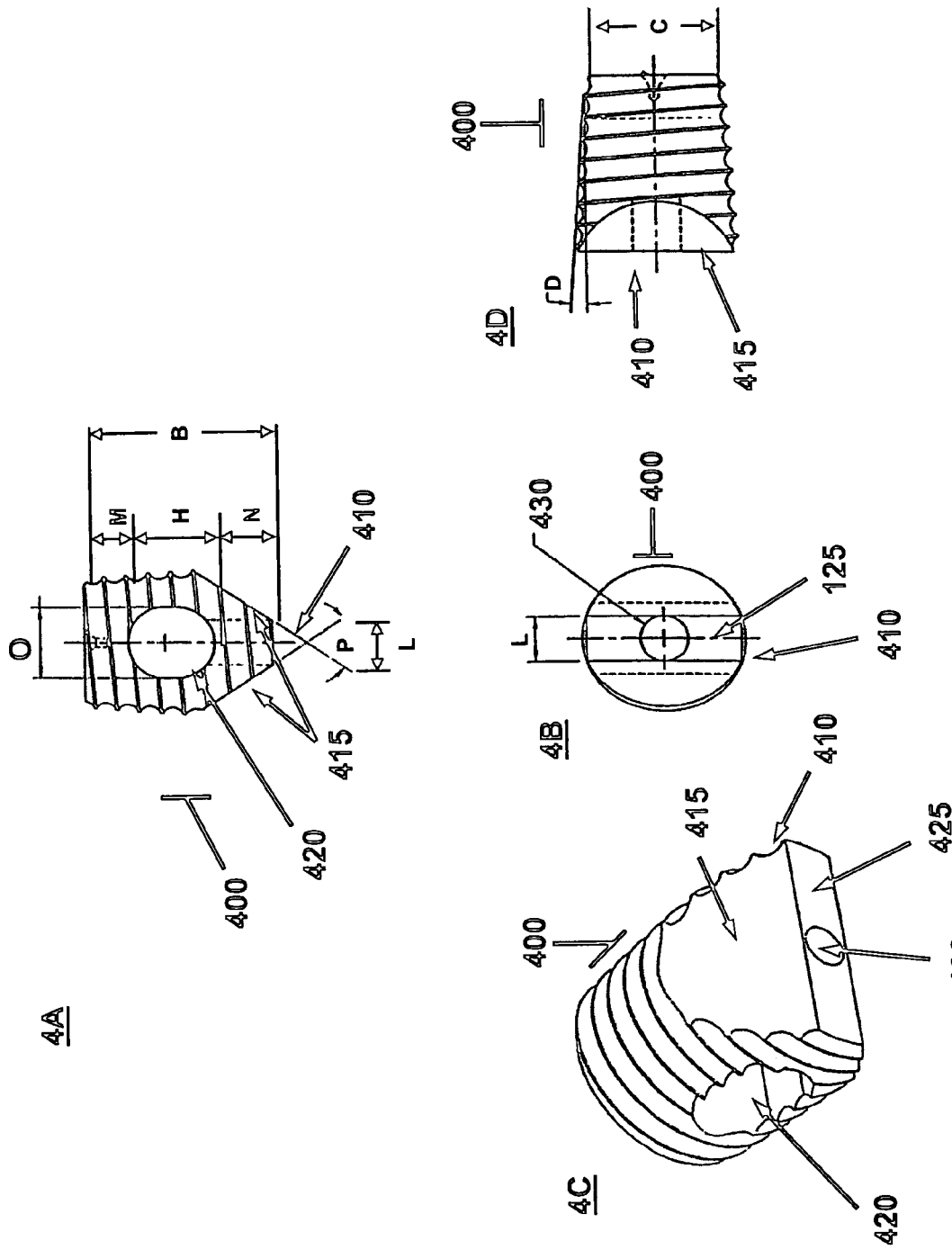
FIG. 4 shows a further embodiment of the subject implant that comprises a wedge-like end to aid in manipulating the implant.

In FIGS. 3A–D, there is shown a further embodiment 300 of the subject implant that is similar to embodiment 200 except that the channel 320 is oval in shape and the thread profile is slightly modified. The oval shape of the channel 320 is achieved by drilling a circular hole through the implant, and then drawing an appropriately dimensioned broach through the circular hole. Preferably, the broach has disposed thereon cutting teeth which change in shape as the diameter of the broach increases from a circular to an oval circumference. Embodiment 300 also comprises a machining attachment hole 310. Those dimensions noted in FIGS. 3A–D have similar values to that described above for embodiment 200 unless otherwise indicated. Dimension H comprises the length of the channel 320 which can range from about 4 to about 8 mm. It represents the angular relation of the holes 305 from the center axis of the implant. As shown, holes 305 are preferably placed 45 degrees above and below the x-axis. FIG. 3B shows the thread profile comprising a ridge J, which can range from about 0.05 mm to about 0.15 mm. Further, embodiment 300 comprises a machining attachment hole 310.

FIGS. 4A–D, show a further embodiment 400 of the subject implant which comprises oblique sides 415 thereby forming a "roof-top" or wedge-like shape on end 410 of the implant to engage a securing device, wherein the securing device is shaped to conform to end 410. Embodiment 400 comprises a channel 420. Further, the dimensions noted in FIGS. 4A–D have the same values as above, unless otherwise indicated. Embodiment 400 comprises a substantially planar or flat end 425 having a dimension L toward which oblique sides 415 slope and connect. Dimension L preferably ranges from 0.5 to about 5 mm. A securing device hole 430 is formed into the wedge end which is designed to engage to a securing device to thereby further stabilize the implant on the securing and driver device during implantation. Dimensions M and N preferably range from about 0.5 mm to about 7 mm. More preferably, dimension N is equal to or larger than dimension M. Wedge angle P preferably ranges from about 45 to about 90 degrees, and preferably is set to a standard style angle to match a reciprocal angle on a driver tool.

It is appreciated in the art that human donor tissue is extremely limited in supply. Thus, it is always advantageous to develop methods of maximizing the use of donor tissue. With this goal in mind, it was discovered that the use of the natural architecture of certain bones in the body are suitable for providing a wedged end as described above for embodiment 400. For example, the tibia comprises an anterior ridge along a substantial portion of its length. It was found that excising block sections along such a ridge can provide oblique sides, thereby avoiding having to machine and discard precious bone material to produce such oblique sides, while preserving donor bone stock for other applications. Where donor bone is less scarce, as in the use of xenograft bone stock, (including but not limited to bovine, ovine, equine, canine or the like) or if allograft bone is in abundant supply, use of the wedge shaped driving structure is less critical. Where used, however, the wedge-shaped driving structure fits conveniently into a complementary driver device for rotation of the implant.

Figure 13:
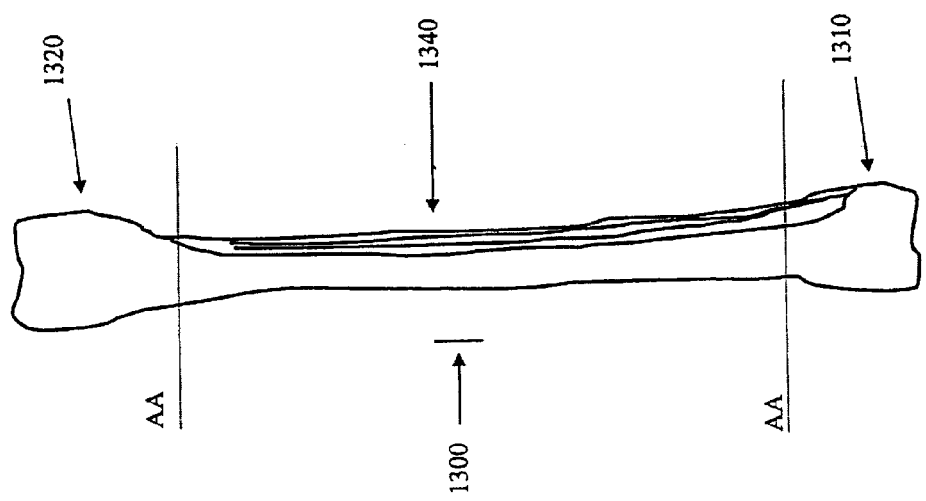
FIG. 13 depicts an example of a bone that is an appropriate source for deriving an implant having a wedge-like end.
Figure 14:
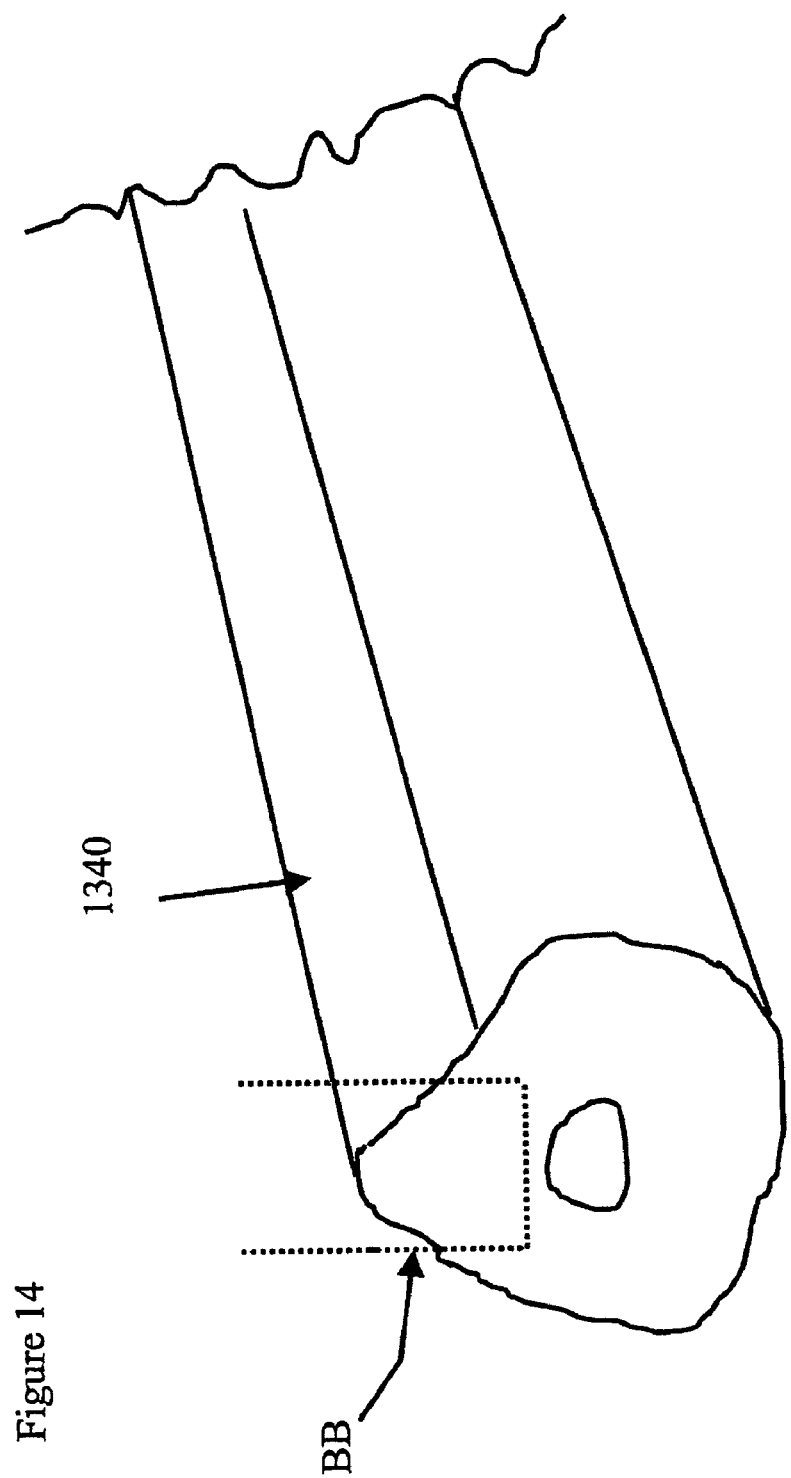
FIG. 14 represents a schematic for procuring a bone block from the bone depicted in FIG. 13, which can then be machined to form an implant according to the teachings of the subject invention.

In an alternative embodiment, as shown in FIGS. 13 and 14, a method of procuring the subject implant comprises obtaining a long bone, such as the tibia 1300, and cutting off the ends 1310 and 1320 from the elongated central portion (dashed lines AA). FIG. 14 shows an end-view of the resulting central portion section produced after excision of the end portions 1310 and 1320. At this point, sections (dashed lines BB) along the ridge 1340 of the tibia are excised which comprise a wedge end as a result of the natural architecture of the bone. Those skilled in the art will understand that this method can be applied to other bones in the body having a desired architecture.

Figure 5:
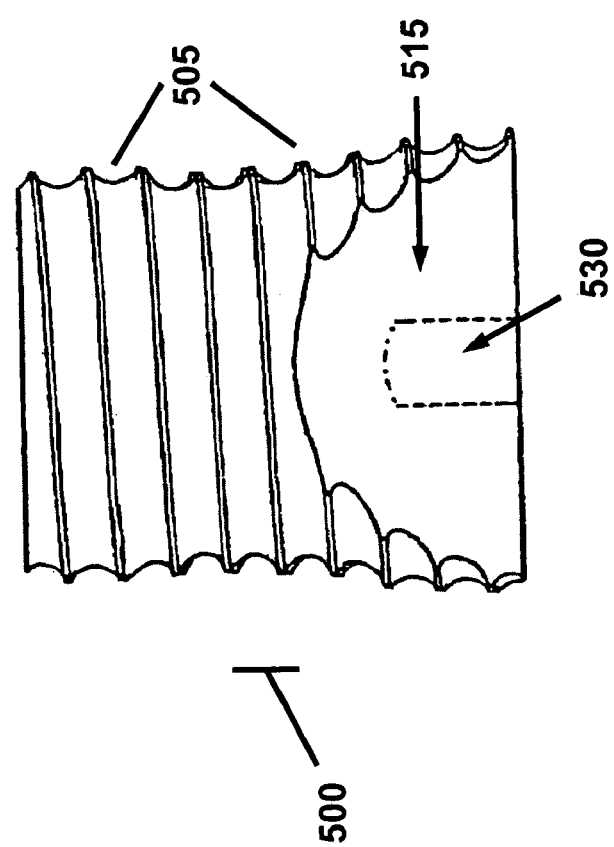
FIG. 5 shows a further embodiment of the subject implant that tapers from one end to the other but has a region in the middle of the implant that is more narrow than either end.

In FIG. 5, there is shown a further embodiment 500 of the subject implant that tapers from one end to the other but has a region in the middle of the implant 505 that is more narrow than either end. Embodiment 500 also preferably comprises oblique sides 515 and a securing device hole 530.

Figure 6:
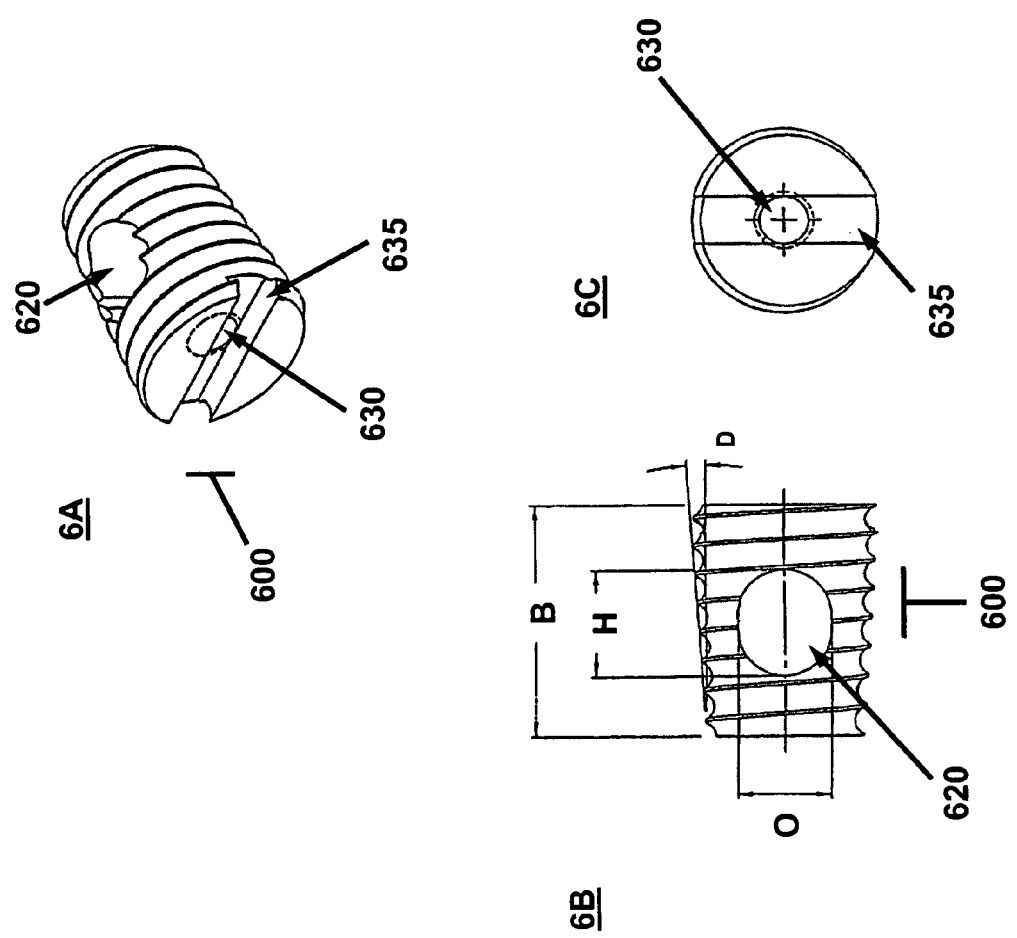
FIG. 6 shows a further embodiment of the subject implant that comprises a slot formed on the wider of the two ends.

In FIGS. 6A–C, there is shown another embodiment 600 of the subject implant having a slot 635 formed on the wider of the two ends of the implant. The slot 635 is designed to engage a securing and driving device, such as, for example, a flat-head screwdriver. As in other embodiments, embodiment 600 comprises a channel 620 and a securing device hole 630. Dimensions B, D, H, and O shown in FIGS. 6A–C, have similar values as described above.

Figure 7:
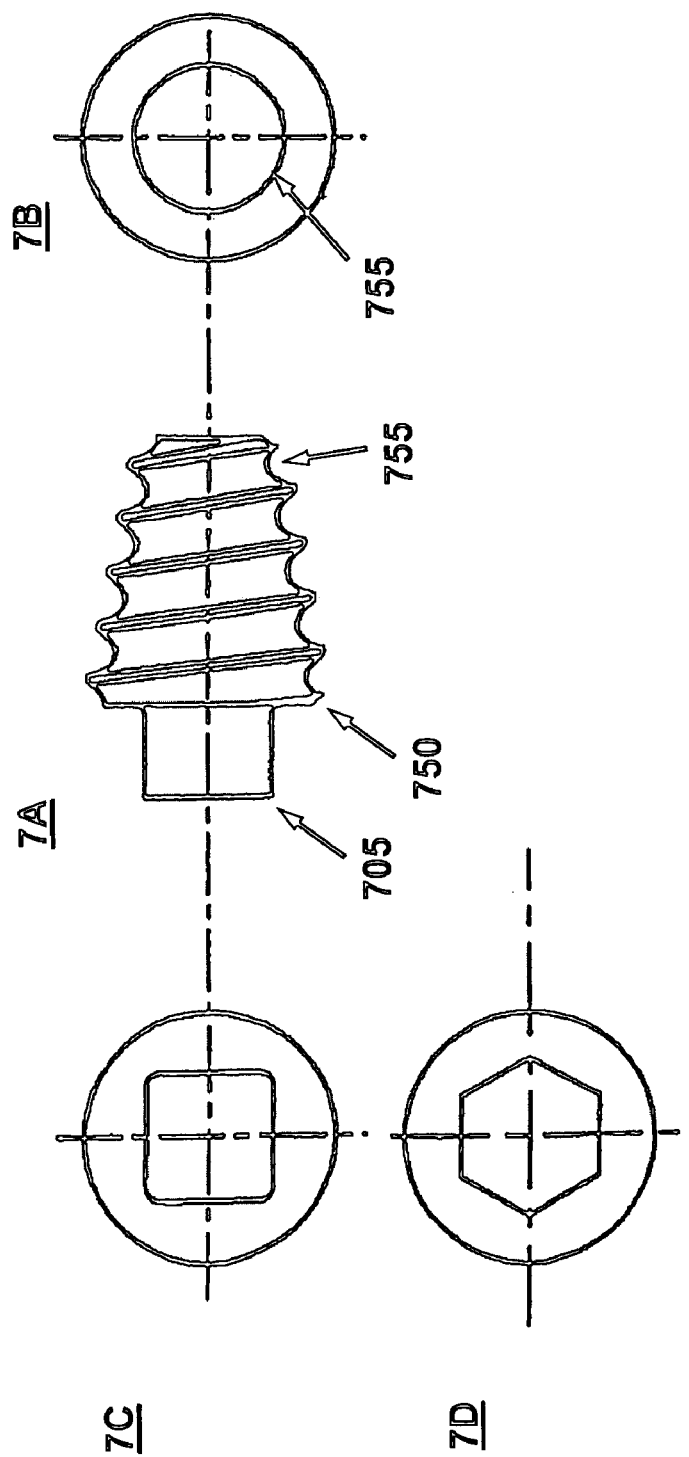
FIG. 7 shows an end-view (FIGS. 7B–C) and side view (FIG. 7A) of several drives for securing the subject implant into place.

In FIGS. 7A–D, there are shown further embodiments of the subject implant that comprises a peg 705 contiguous with and extending from end 750, the wider of the two ends of the implant. The peg acts as driver to turn and secure the implant when engaged to a securing device. The peg device may be round for being driven by a collet, or may be square or otherwise shaped for secure torquing by a reciprocal driving means. FIG. 7B shows an end-view of the narrower end 755. FIGS. 7C and D show various alternatives for the shape of the peg, e.g., square and hexagonal. The skilled artisan will appreciate other appropriate shapes can be used, e.g. octagonal, triagonal, etc. In addition, it will be appreciated that the drive means may be recessed into the implant and driven by an appropriately shaped driver.

Figure 8:
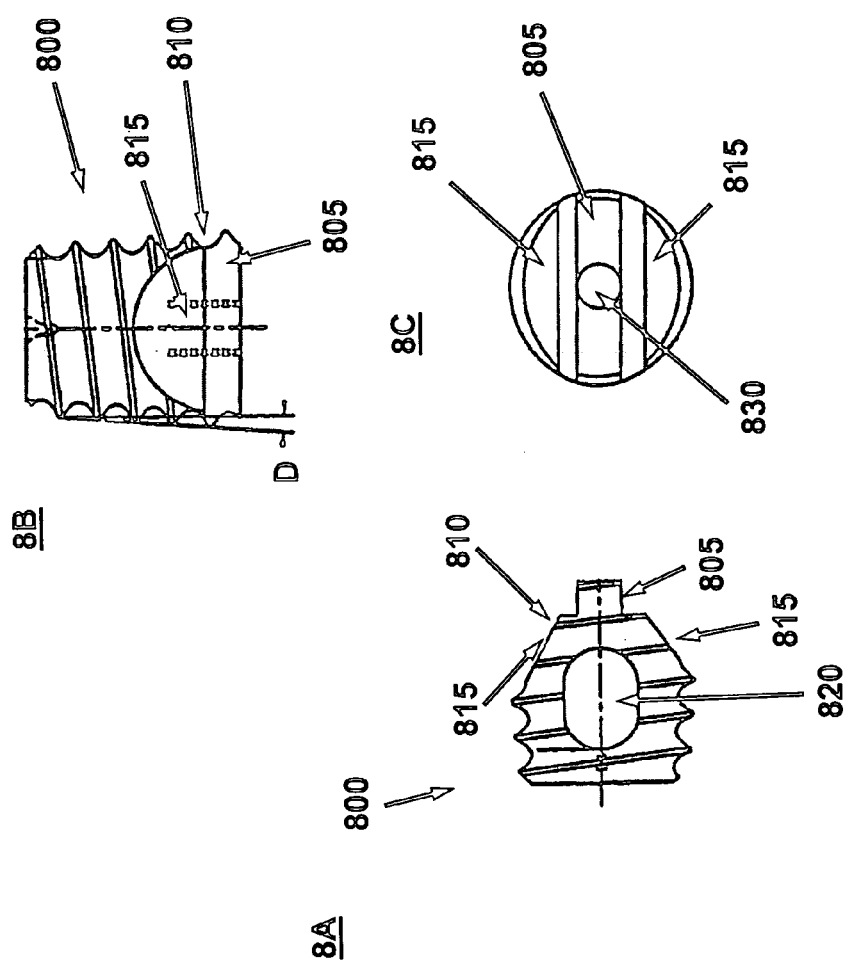
FIG. 8 shows side views (FIGS. 8A–B) and end view (FIG. 8C) of a further embodiment of the subject implant.

In FIGS. 8A–C, there is shown another embodiment 800 of the subject implant that comprises both a wedge-like end 810 and a raised vertex 805 to further aid in engaging a securing device. Embodiment 800 comprises a securing device hole 830 as well. FIG. 8C shows an end-view of embodiment 800 showing the raised vertex 805, securing device hole 830, and the oblique sides 815. The value of D is the same as that described above. Preferably, as shown in FIG. 8A, the implant comprises a channel 820.

Figure 9:
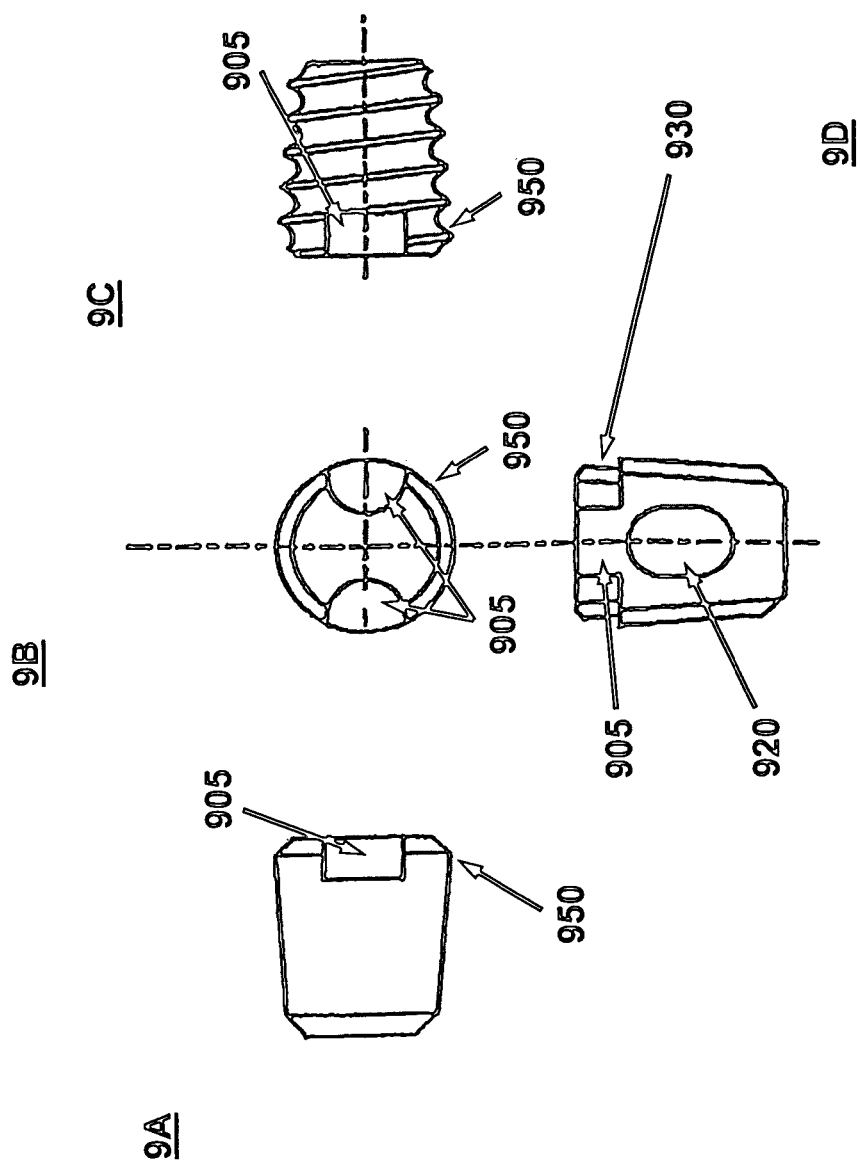
FIG. 9 shows a further embodiment of the subject implant that comprises pinch cut out for engaging a securing device.

FIGS. 9A–C show a further embodiment 900 of the subject invention that comprises two or more pinch cut outs 905 from the edge of the wider of the two ends 950 of the implant. The pinch cut outs 905 act to engage a securing device for securing the implant in the patient. FIG. 9A shows a version of the embodiment 900 that does not have threads disposed on its surface. FIG. 9B shows an end-view of the wider end 950, which depicts two pinch cut outs 905 positioned on opposing sides of the implant. FIG. 9C shows a threaded embodiment. FIG. 9D shows an embodiment that comprises a channel 920 and a narrower stepped portion 930 at its wider end 950.

Those skilled in the art will appreciate that the subject implant does not necessarily comprise threads. However, threads are preferred in most cases, as they aid in securing the implant in the patient. Rotation of the subject implant results in the threads digging into the adjacent bones thereby forming a tight contact.

Figure 10:
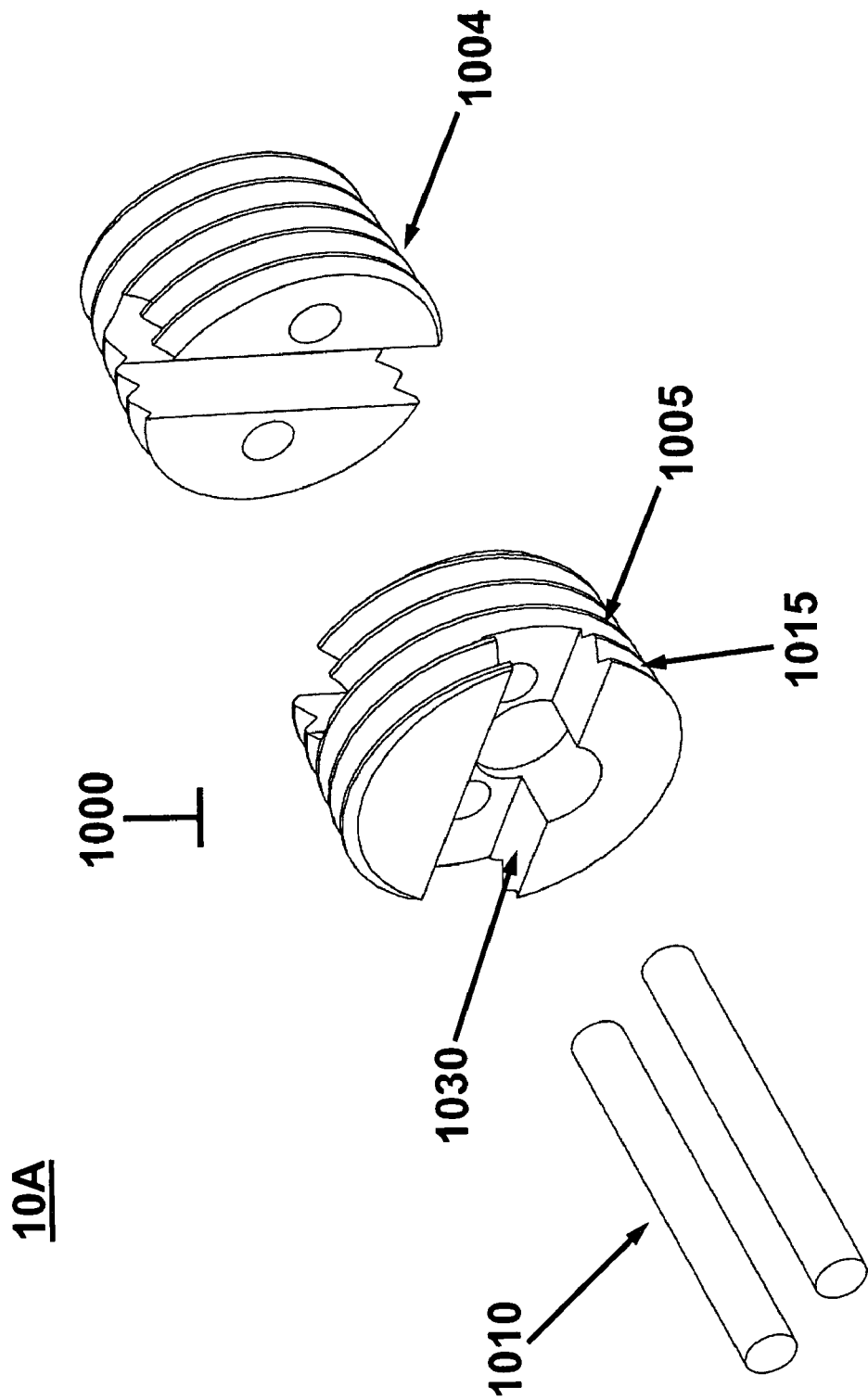
FIG. 10 shows a perspective view of another embodiment of the subject invention that comprises a number of separate pieces (FIG. 10A) that are assembled into a single unit (FIG. 10B).
Figure 10:
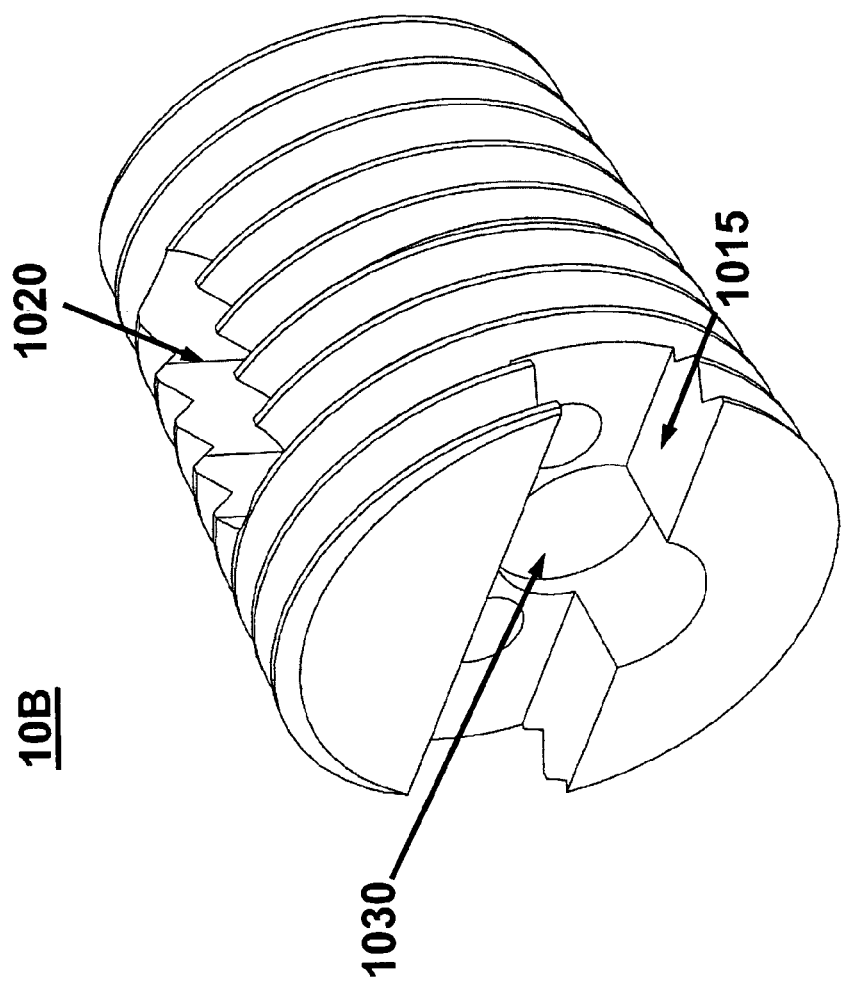

In FIGS. 10A–B, there is shown another embodiment 1000 of the subject implant that is comprised of two or more sections that are assembled into a single unit. Embodiment 1000 comprises a first section 1004 and a second section 1005 that are placed contiguous to each other and then secured together by pins 1010. The pins 1010 may be formed from any appropriate material, including but not limited to cortical bone, titanium, stainless steel, hydroxyapatite, bioactive glass, polylactic acid and like polymers. The second section has a slot 1015 formed thereon for engaging a securing device, as well as a securing device hole 1030 for further stabilization on the securing device during implantation. FIG. 10B shows the embodiment 1000 as assembled. In addition to the slot 1015 and the securing device hole 1030, FIG. 10B illustrates the formation of a channel 1020 when the implant is assembled. Those skilled in the art equipped with the teachings herein will appreciate that the second section 1005 comprising the slot 1015 could be configured to have formed thereon any of the other driver means described herein, e.g., wedge, raised ridge, peg, pinch, 4-pin, etc.

Figure 11:
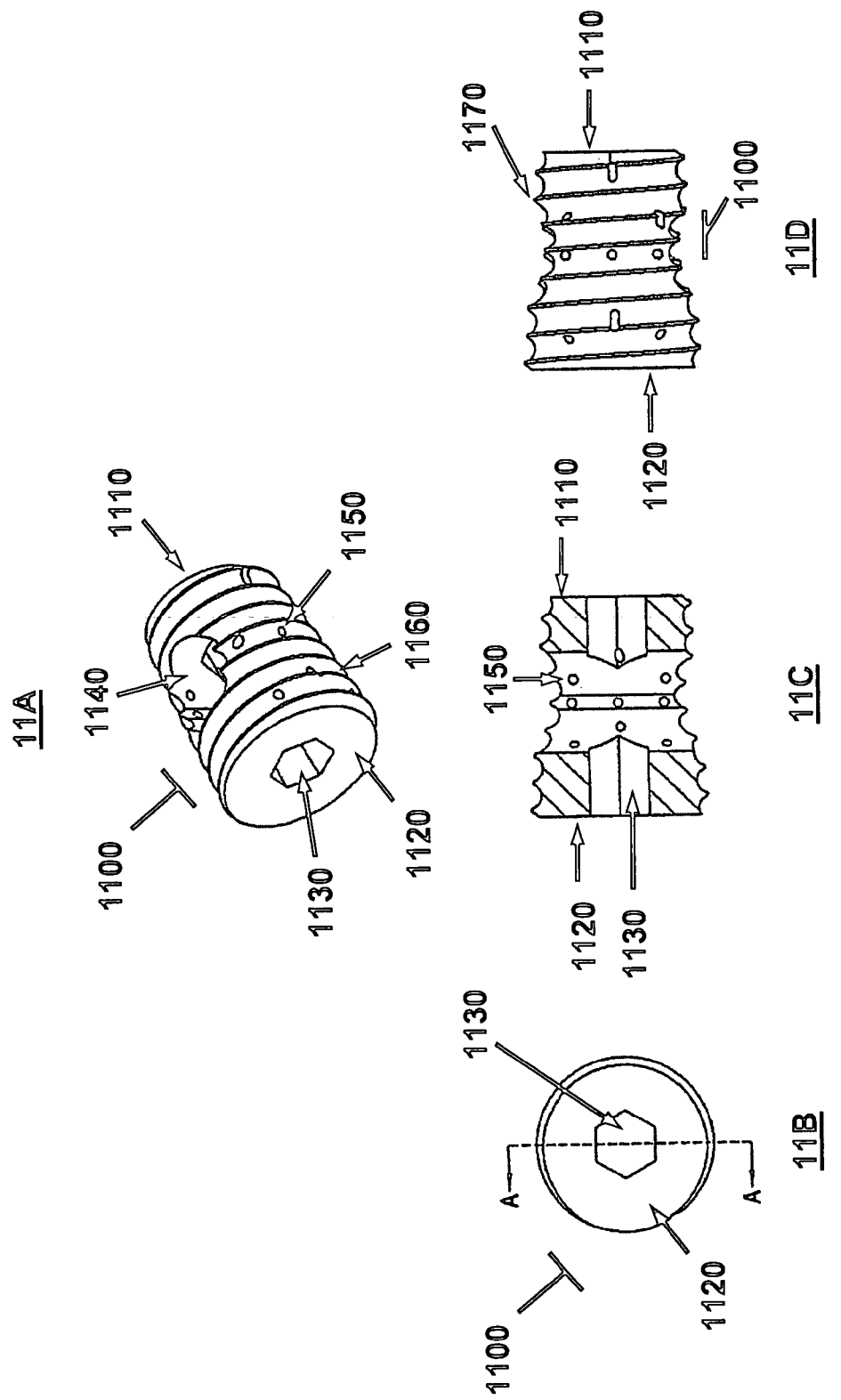
FIG. 11 shows a perspective view (FIG. 11A), an end-view (FIG. 11B), a cross-sectional view (FIG. 11C), and a side view (FIG. 11D) of another embodiment of the subject implant that is perforated to facilitate delivery of biologically active substances.

FIG. 11A shows a perspective view of further embodiment 1100 of the subject implant, having a tapered body resulting in a smaller diameter for the front end 1110, and a larger diameter for the back end 1120. The back end 1120 comprises a hex drive 1130 formed therein for insertion and rotation of the implant. Implant 1100 defines a channel 1140 for use of packing biologically active substances. Holes 1150, which radiate from the channel 1140 to the cortical surface 1160, allow the biologically active substances to penetrate through the entire implant 1100. FIG. 11B is an end plan view of implant 1100 showing the back end 1120 along with the hex drive 1130. FIG. 11C depicts a transverse section of implant 1100 along the AA axis shown in FIG. 11B. The hex drive 1130 is shown running from the front end 1110 to the back end 1120. FIG. 11D shows a side view of implant 1100, holes 1150, and screw threads 1170 which are inscribed from the front end 1110 to the back end 1120. The screw threads 1170 ease insertion and help to hold the implant in place.

Figure 12:
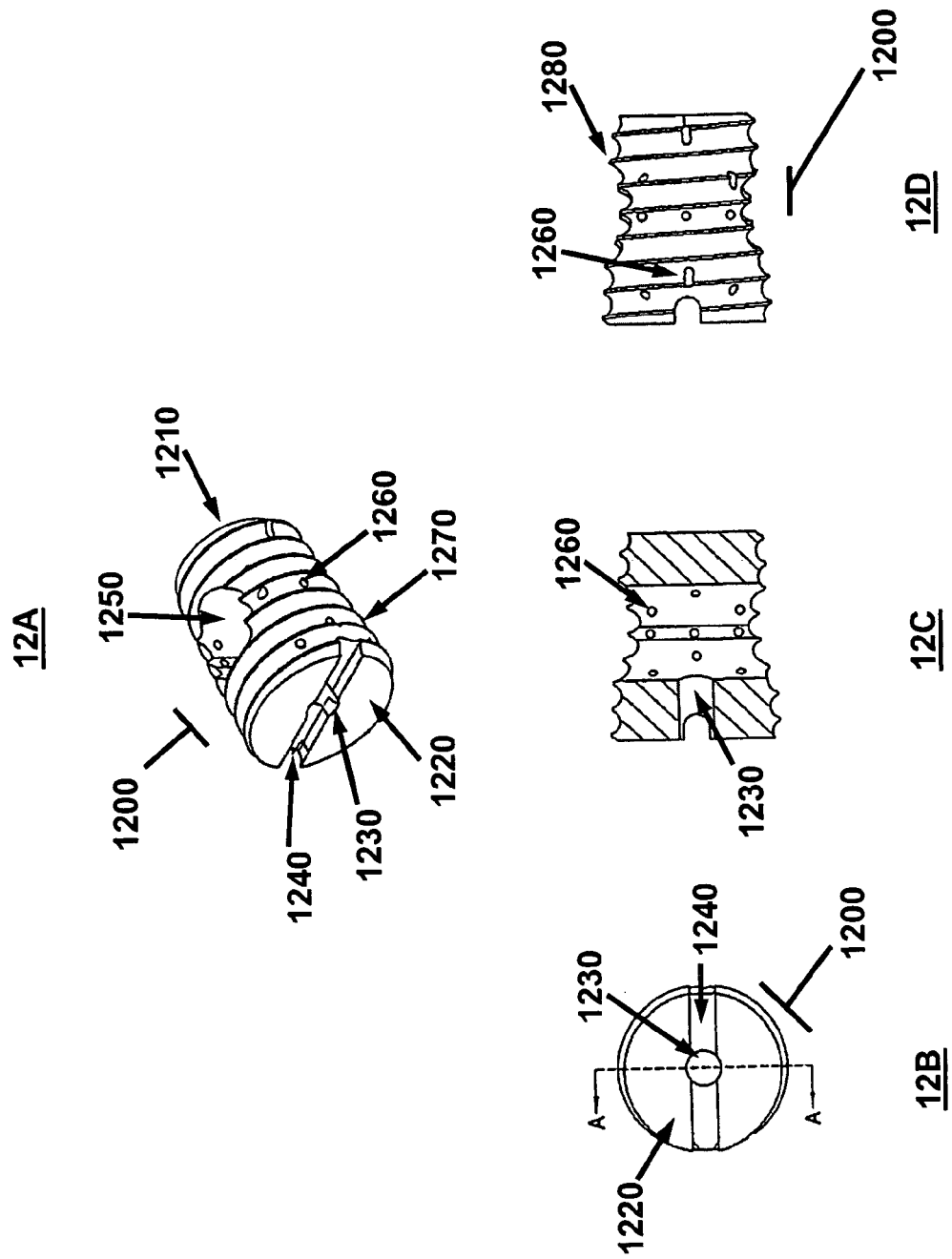
FIG. 12 shows a perspective view (FIG. 12A), an end-view (FIG. 12B), a cross-sectional view (FIG. 12C), and a side-view (FIG. 12D) of an embodiment of the subject implant which is a variation of the embodiment shown in FIG. 11.

FIGS. 12A–12D show an alternate embodiment of the cervical tapered dowel depicted in FIGS. 11A–11D. FIG. 12A shows a perspective view of implant 1200, having a tapered body resulting in a smaller diameter for the front end 1210 and a larger diameter for the back end 1220. The back end 1220 contains an instrument hole 1230 along with a score mark 1240 for use with an insertion device to provide torque to the implant. Implant 1200 contains a channel 1250 for packing biologically active substances along with holes 1260 that radiate from the channel 1250 to the cortical surface 1270. FIG. 12B is an end plan view of implant 1200 showing back end 1220 along with the instrument hole 1230 and the score mark 1240. FIG. 12C depicts a transverse section of implant 1200 along the AA axis shown in FIG. 12B. The instrument hole 1230 is shown extending partially through the implant into the channel 1250. FIG. 12D shows a side view of implant 1200. The screw threads 1280 ease insertion and help the implant retain its position once implanted.

It will further be appreciated from the present disclosure that the implant may be contacted with cells prior to implantation. For example, bone implants according to this invention may be cultured with stem cells, fibroblasts, muscle cells, neuronal cells or the like or simply contacted therewith or be infused therewith prior to implantation. Preferably, the cells that are contacted with the implant are stem cells, such as those known in the art or which become known hereafter. For example, human mesenchymal or other stem cells, such as those disclosed in any of U.S. Pat. Nos. 5,486,359; 5,811,094; 5,197,985; 5,591,625; 5,733,542; 5,736,396; 5,908,784; 5,942,255; 5,906,934; 5,827,735; 5,962,325; 5,902,741; 4,721,096; 4,963,489; (all of which are hereby incorporated by reference), may be contacted with, infused into or cultured on the implants of the present invention. The plurality of holes in the implant of this invention thus permit for interpenetration of such cells into the interior of the implant prior to implantation, and from the interior of the implant, to assist in remodeling, subsequent to implantation.

Alternatively, perforations or holes can be formed in the subject implants, which can control and improve the release and delivery of biologically active substances loaded in the channel, or otherwise infused, embedded or coated on or in the implants. Naturally, the rate of release will be dependent on the size and number of holes provided. As discussed above, the channel of the subject dowels can be packed with various biologically active substances, including, but not limited to, growth factors, antibiotics, nucleic acids, proteins, peptides, antineoplastics, and anti-inflammatory compounds, and the like. Furthermore, the plurality of holes taught herein can facilitate the migration and growth of cells and tissues into the implant. It will be appreciated that any appropriate carrier may be used in association with these biologically active substances, including, but not limited to, gelatin, collagen, mixtures thereof, synthetic compositions, biologically resorbable pastes and the like. Furthermore, the composition may comprise a bone paste composition comprising cortical bone chips, cancellous bone chips, demineralized bone matrix powder (DBM), bioactive glass or other ceramics, growth factors, nucleic acids, proteins, peptides, carbohydrates, lipids and the like. Preferably, the substance packed in the canal is an osteogenic substance and/or comprises tissue regenerating growth factors. See, for example, WO98/40113, herein incorporated by reference. Optionally, or in addition to packing the canal, the subject implants can be infused, soaked and/or coated with various biologically active substances.

EXAMPLE

Procedure for Procuring an Implant Having a Wedged End from a Human Tibia

Equipment

Sherline Mill with 3" vice attached to cross table

Modified Sherline machining lathe with tail stock and tooling bit

Modified Sherline lathe with threading attachment

Core Cutters, 12 mm and 14 mm 3 mm drill bit

0 starter drill

Dial calipers

Fine toothbrush

Scraping tool

Procedure

An appropriate size cutter was loaded in the chuck of the Sherline mill. The tibia segment was clamped in the vice on the mill table with the anterior of the segment facing up and aligned properly and tightened, and the cutter was aligned to the segment. The motor assembly was adjusted to about 200 RPM, and the cutter was lowered down to the bone and cut through the segment. The cutter was retracted to its original position and the cut dowel was removed from the cutter. The foregoing was repeated until all of the dowels were cut.

To form the wedge end of the dowel, a cut dowel as described above was placed with the anterior end facing the tooling bit in the chuck of the machining lathe and tightened. The lathe motor was turned on and the end of the dowel was machined to form 3.5 mm oblique side on the end. Using the center drill in the tail-stock, a starter hole was drilled in the end of the dowel. This operation was repeated until all of the dowels were machined with the oblique side and had the starter hole drilled therein.

The ends of machined dowels opposite the oblique sides were flattened and cancellous bone was removed. To accomplish this, each dowel was individually placed into the chuck with the posterior end of the dowel facing the tooling bit and tightened. The end of the dowel was machined until all the cancellous bone was removed and the dowel was flat. The dowel was then removed from the chuck and measured to determine if the length was at a desired length and to determine whether more bone needed to be removed. Using the center drill in the tail stock, a starter hole in the flattened end of the dowel was drilled. This procedure was repeated for all of the machined dowels. Next, the 3 mm drill bit was secured in the chuck in the tail-stock and tightened. A dowel with the 3.5 mm flat was placed in the chuck facing the drill bit and tightened. The tail-stock was advanced forward until the tip of the drill bit was about 1 mm from the end of the dowel and the tail-stock was tightened to the lathe bed. The motor was activated and the drill bit was advanced into the dowel to form a hole 6 mm in depth. This procedure was repeated for all of the dowels.

The dowels having the oblique sides, flattened end and holes drilled on both ends were then subjected to the threading lathe. The dowel was placed in the threading lathe and tightened. The air motor was activated with the milling cutter attached and advanced into the dowel until lightly touching the dowel. The threading handle was turned to move the cutter assembly to the right until it cleared the dowel. The cutter was advanced forward to remove the desired amount of bone to achieve the desired dowel diameter. The foregoing procedure was repeated for all of the dowels. Using a burring tool or a scraper, any burrs present were removed from the dowel. A fine tooth brush was used to brush the threads on the dowel to remove any fine burrs.

The teachings of all of the references cited throughout this specification are incorporated herein by this reference to the extent that they are not inconsistent with the teachings herein. Thus, for example, a device made from metal is known for application to the cervical spine (see U.S. Pat. No. 5,782,919; U.S. Pat. No. 5,669,909, herein incorporated by reference for this purpose). The present invention provides an improvement to such devices in that the bone material of the present implant is remodelable, such that autogenous bone replaces implant bone over time to induce a permanent fusion, while metallic implants frequently require removal or cause stress shielding, ultimately causing the implant to fail. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An assembled helically threaded implant for implantation between adjacent vertebrae in the spine of a patient comprising two or more helically threaded sections of cortical bone, each threaded section having a circular cross section, each two sections of cortical bone are joined together in tandem by two pins to form an implant that is longer than it is wide, said pins interconnecting opposing holes in said threaded sections to form an elongated body from about 5 mm to about 25 mm in length wherein all longitudinal surfaces are continuously tapered and also threaded, said elongated body also having a first end having a first diameter for initially engaging adjacent vertebrae and an opposing second end having a second diameter that is larger than said first diameter, said second end also including a shape for engaging a driving and securing device, said pins conveying torsional load between said threaded sections as said threaded sections are rotatedly advanced between said vertebrae.

2. The implant of claim 1, having two threaded and continuously tapered sections of cortical bone.

3. The implant of claim 1, wherein said second end includes a slot formed thereon.

4. The implant of claim 1, wherein said second end includes a square driver.

5. The implant of claim 1, wherein said second end includes a hexagonal driver.

6. The implant of claim 1, wherein said second end includes two or more pinch cut outs.

7. The implant of claim 1, wherein said second end includes two pinch cut outs.

* * * * *